United States Patent
Cohen et al.

(10) Patent No.: US 10,137,158 B2
(45) Date of Patent: Nov. 27, 2018

(54) USE OF PHOTOSYNTHESIS TO REBALANCE ISCHEMIA BIOENERGETICS

(71) Applicant: The Board of Trustees of the Leland Stanford Junior University, Stanford, CA (US)

(72) Inventors: Jeffrey E. Cohen, Philadelphia, PA (US); Andrew B. Goldstone, San Francisco, CA (US); Y. Joseph Woo, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 130 days.

(21) Appl. No.: 15/136,612

(22) Filed: Apr. 22, 2016

(65) Prior Publication Data

US 2016/0310547 A1 Oct. 27, 2016

Related U.S. Application Data

(60) Provisional application No. 62/152,716, filed on Apr. 24, 2015.

(51) Int. Cl.
| *A61K 35/748* | (2015.01) |
| *A61N 5/06* | (2006.01) |
| *C12N 1/20* | (2006.01) |
| *A61K 41/00* | (2006.01) |
| *A61N 5/067* | (2006.01) |
| *A61K 35/12* | (2015.01) |

(52) U.S. Cl.
CPC ............ *A61K 35/748* (2013.01); *A61K 41/00* (2013.01); *A61N 5/0601* (2013.01); *A61N 5/062* (2013.01); *C12N 1/20* (2013.01); *A61K 2035/128* (2013.01); *A61N 2005/063* (2013.01); *A61N 2005/067* (2013.01); *A61N 2005/0651* (2013.01)

(58) Field of Classification Search
None
See application file for complete search history.

(56) References Cited

U.S. PATENT DOCUMENTS

| 2005/0136092 A1* | 6/2005 | Rotem | A61F 2/022 424/423 |
| 2010/0184169 A1* | 7/2010 | Roberts | C12N 1/20 435/134 |
| 2014/0371666 A1* | 12/2014 | Stern | C12M 21/02 604/24 |

FOREIGN PATENT DOCUMENTS

WO WO-2013049107 A2 * 4/2013 ........... A61K 9/4816

* cited by examiner

*Primary Examiner* — Scott Long
*Assistant Examiner* — Nghi V Nguyen
(74) *Attorney, Agent, or Firm* — Pamela J. Sherwood; Bozicevic, Field & Francis LLP

(57) ABSTRACT

Compositions and methods are provided for photosynthetic correction of metabolic imbalances that occur in ischemic conditions. In the methods of the invention, an ischemic or potentially ischemic tissue is contacted with an effective dose of a photosynthetic system in the presence of a light source, where the dose or concentration is sufficient to increase oxygenation and simple sugar supply of the targeted tissue or organ.

10 Claims, 8 Drawing Sheets
(6 of 8 Drawing Sheet(s) Filed in Color)

Flow probe on ascending aorta

Ischemic LV

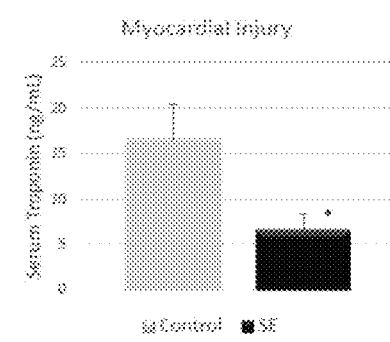
Figure 4A
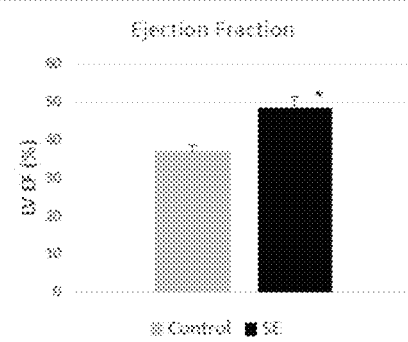
Figure 4B
Figure 4C
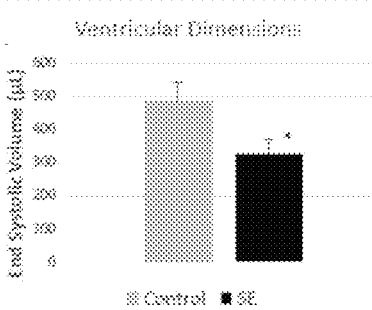
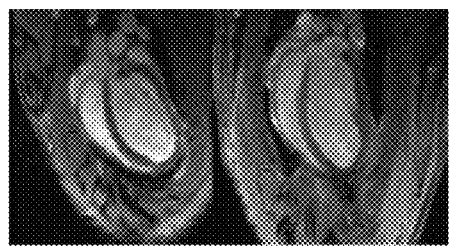
Figure 4D
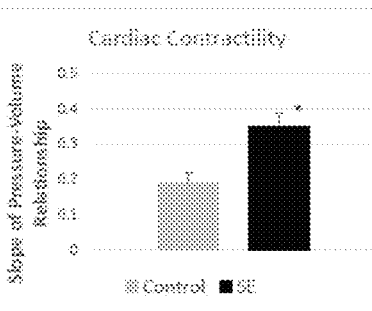
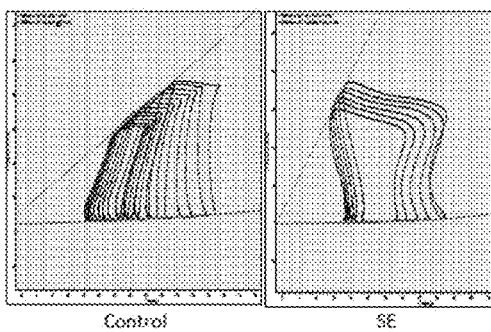
Figure 4E
Figure 4F

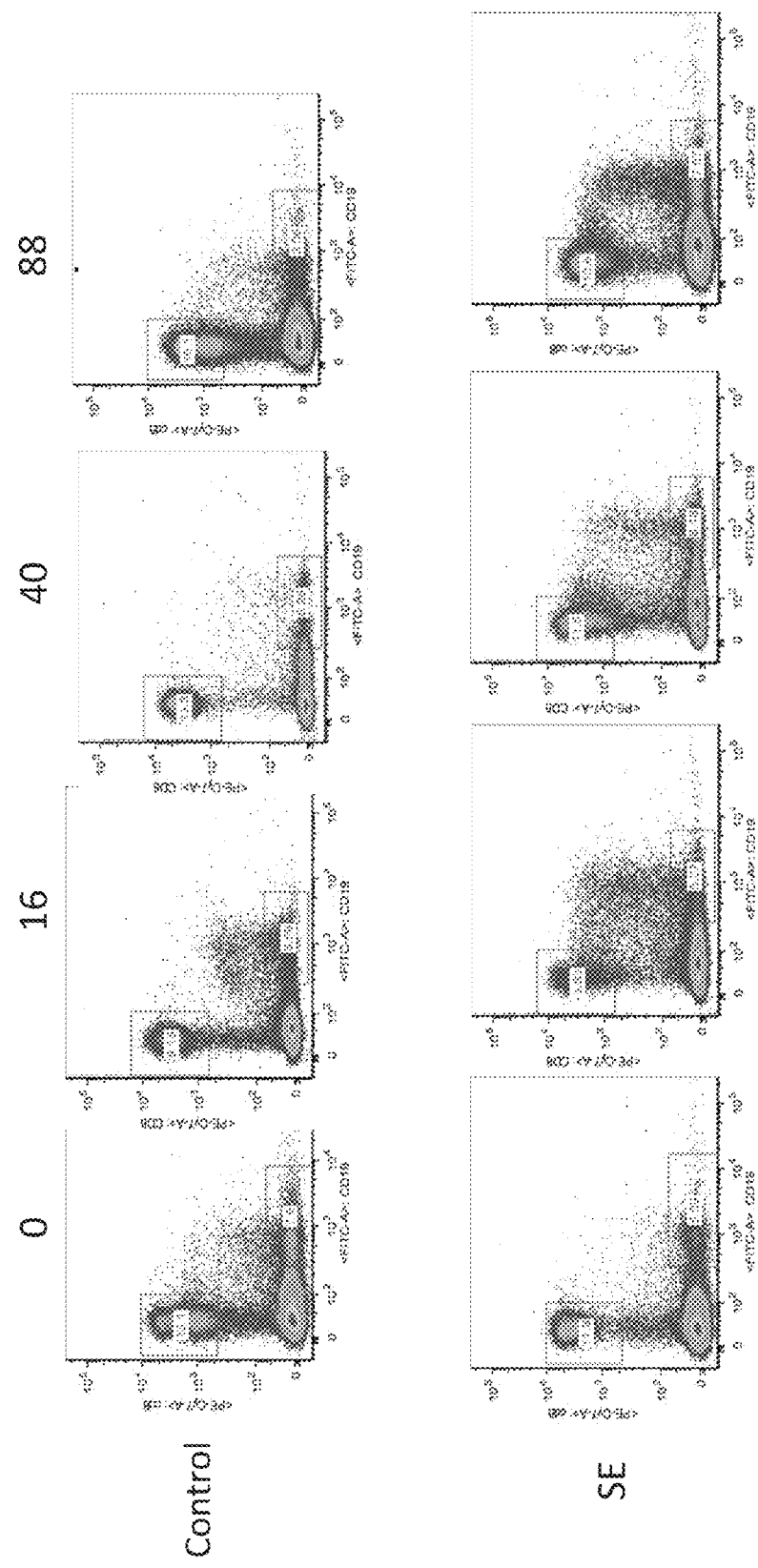

USE OF PHOTOSYNTHESIS TO REBALANCE ISCHEMIA BIOENERGETICS

BACKGROUND OF INVENTION

In mammalian cells and organs, oxygen plays a vital role in bioenergetics, primarily through oxidative phosphorylation in mitochondria. In these organelles, an electron transport chain establishes a proton gradient across the inner membrane that drives phosphorylation of ADP to ATP. Oxygen acts as the final electron acceptor in the chain, to form water. However, within the mitochondria, the electron transport system (ETS) has also been well-studied as a source of reactive oxygen species (ROS) production with superoxide radicals forming spontaneously at complexes I, II, and III via the swift addition of leaking electrons to an incompletely reduced oxygen. During ischemia, mitochondrial ROS is increased from several sites, largely a result of oxidative damage to ETS and to enzymes in the matrix. Upon reperfusion following ischemia, a burst of ROS from the ETS is a well-characterized phenomenon that can have deleterious effects.

Normally sufficient $O_2$ is provided by circulated blood, but there are a number of clinically relevant conditions in which acute or chronic ischemia results from inadequate blood flow. When oxidative stress is prolonged or of high enough magnitude in disease settings, cells respond in a manner that results in a maladaptive phenotype. Overwhelming levels of oxidative stress in disease states leads to alterations in myocyte mitochondrial function and polarity, cell death, and hyper-activation of neutrophils/macrophages with subsequent fibrosis.

Ischemia is a vascular disease involving an interruption in the arterial blood supply to a tissue, organ, or extremity that, if untreated, can lead to tissue death. It can be caused by embolism, thrombosis of an atherosclerotic artery, or trauma. Venous problems like venous outflow obstruction and low-flow states can cause acute arterial ischemia. Many tissues can be impacted by ischemic conditions, including the heart, large and small intestines, brain, limbs, kidneys, liver, etc.

Since oxygen is carried to tissues in the blood, insufficient blood supply causes tissue to become starved of oxygen. In the highly aerobic tissues of the heart and brain, irreversible damage to tissues can occur in as little as 3-4 minutes at body temperature. The kidneys are also quickly damaged by loss of blood flow. Tissues with slower metabolic rates may undergo irreversible damage after 20 minutes. In the absence of oxygen, ATP production in a mammalian cell is considerably less efficient, and the balance of reactants is undesirably skewed to an excess of $CO_2$. Without immediate intervention, ischemia may progress quickly to tissue necrosis and gangrene within a few hours.

Restoration of blood supply to ischemic tissues can cause additional damage known as reperfusion injury that can be more damaging than the initial ischemia. Reintroduction of blood flow brings oxygen back to the tissues, causing a greater production of free radicals and reactive oxygen species that damage cells. It also brings more calcium ions to the tissues causing further calcium overloading and can result in potentially fatal cardiac arrhythmias and also accelerates cellular self-destruction. The restored blood flow also exaggerates the inflammation response of damaged tissues, causing white blood cells to destroy damaged cells that may otherwise still be viable.

Among ischemic conditions, acute coronary syndromes (ACS) result from acute obstruction of a coronary artery. Consequences depend on degree and location of obstruction and range from unstable angina to non-ST-segment elevation MI (NSTEMI), ST-segment elevation MI (STEMI), and sudden cardiac death. In the US, about 1.5 million myocardial infarctions (MIs) occur annually, resulting in death for 400,000 to 500,000 people. These syndromes usually occur when an acute thrombus forms in an atherosclerotic coronary artery. Initial consequences vary with size, location, and duration of obstruction and range from transient ischemia to infarction.

Ischemic, but not infarcted, tissue has impaired contractility and relaxation, resulting in hypokinetic or akinetic segments; these segments may expand or bulge during systole (called paradoxical motion). The size of the affected area determines effects, which range from minimal to mild heart failure to cardiogenic shock. Some degree of heart failure occurs in about two thirds of hospitalized patients with acute MI, which is myocardial necrosis resulting from abrupt reduction in coronary blood flow to part of the myocardium. Infarcted tissue is permanently dysfunctional; although there is a zone of potentially reversible ischemia adjacent to infarcted tissue.

Over the past decades, research and innovation have enabled advances in preventative, pharmacologic, and surgical strategies to greatly augment the clinician's ability to treat once devastating acute and chronic cardiac events. Stemming from these accomplishments, a more recent wave of exploration into cardiac tissue regeneration and angiogenesis has yielded exciting results in preclinical models and early clinical trials. While these myocardial repair strategies for cardiac injury possess great promise and popularity, it remains critical to pioneer alternative and uncharted pathways for the treatment of myocardial injury.

In addition to in vivo ischemic situations, the removal, storage, and transplantation of a solid organ from a donor profoundly alters the homeostasis of the interior milieu of the organ. These effects manifest in the degree to which the return of normal organ function is delayed or prevented after transplantation is completed. The injury an organ sustains during recovery, preservation, and transplantation occurs primarily as a result of ischemia and hypothermia. Techniques for organ preservation serve to minimize this damage to promote optimal graft survival and function.

During ischemia and organ preservation, the glycolytic pathway is shunted to lactate production, as the Krebs tricarboxylic acid cycle (TCA) cycle and mitochondrial respiration are impaired. Mitochondrial dysfunction is responsible for most of the changes in cellular energy associated with ischemia and organ preservation. Much of the injury to transplanted organs occurs not during ischemia, but during reperfusion. This finding has led to many advances in organ preservation aimed at preventing this type of injury. Furthermore, some of the events that occur during reperfusion may result in enhanced immunogenicity of the graft.

The present invention provides novel methods for correcting the metabolic imbalances that result from ischemia. These compositions and methods are of great clinical interest for in vivo and ex vivo methods of treatment.

SUMMARY OF INVENTION

Compositions and methods are provided for photosynthetic correction of metabolic imbalances that occur in ischemic conditions. In the methods of the invention, an ischemic or potentially ischemic tissue is contacted with an effective dose of a photosynthetic system, e.g. isolated chloroplasts, artificial photosynthetic systems, photocatalyst water splitting, photosynthetic microorganisms, etc. in the presence of a light source, where the dose or concentration is sufficient to increase oxygenation and simple sugars (i.e. glucose, fructose, etc.) at the targeted tissue or organ. In some embodiments the photosynthetic system is an effective dose of photosynthetic microorganisms. The tissue may be present in vivo, or ex vivo, e.g. as an isolated organ for transplantation. In some embodiments the photosynthetic microorganism is a single-cell organism, including without limitation cyanobacteria. Specific organisms of interest include without limitation, *Synechococcus* sp., e.g. *Synechococcus elongatus*. The photosynthetic microorganism may express chlorophyll F protein. Preferred photosynthetic organisms have low levels of LPS, e.g. due to low levels in the native organism, due to genetic engineering of the organism to decrease LPS, or due to treating the organism with an agent that blocks LPS.

In some embodiments of the invention, an organ or peripheral tissue in a mammal, including without limitation a mammalian heart, is contacted with an effective dose of a cyanobacteria in the presence of a light source for a period of time during reduced blood flow to the tissue. The period of ischemia may be acute or chronic. In some embodiments, the period of reduced blood flow occurs during a surgical procedure. Although not required, the tissue may be cooled, usually to a temperature higher than conventional cooling, e.g. down to about 20° C., down to about 25° C., down to about 27.5° C., down to about 30° C., down to about 32.5° C., down to about 35° C. The source of light may be ambient light, or may be provided by, for example, a surgically acceptable light source that can be placed in or adjacent to the tissue of interest. Sources of light include, without limitation, LED light sources, infrared light sources, incandescent light sources, halogen lights, etc. In some embodiments the light source is an LED.

For in vivo purposes, the effective dose of the photosynthetic microorganism may be delivered systemically, e.g. by iv injection or locally by direct injection into the affected tissue. When systemically delivered, the microorganism may optionally be substantially cleared from circulation by apheresis and affinity purification, by administration of an antibiotic agent, by introduction of a genetic "kill switch" into the microorganism followed by delivery of an agent that activates the switch; and the like. Alternatively the microorganism may be cleared from circulation by the host system. In many embodiments the circulation will be monitored, e.g. by counting microorganisms present in circulation post-administration to determine if suitable clearance has occurred.

In other embodiments of the in vivo delivery methods, the effective dose of the photosynthetic microorganism is localized by containing the cells in an implantable immunoisolation device. In such a device, the microorganisms are bounded by a semi-permeable membrane allowing transport of $O_2$, ROS, glucose, $CO_2$, etc., but which isolates the microorganisms from the host immune defenses, and which allows ease of removal following the procedure. Such a device may additionally provide an integrated light source, that provides suitable light for photosynthesis. Typically such a device is placed in promixity and fluid connection with the targeted organ for the duration of the procedure or remains in place for long-term treatment of chronic ischemia.

Methods of the invention directed at ex vivo treatment may be performed for the maintenance of tissues and organs for a period of time when the tissue or organ is maintained ex vivo, particularly in the context of organs for transplantation. The photosynthetic microorganisms may be delivered in a device, as described above, or may be suspended in the organ preservation fluid. The fluid may be optimized to allow photosynthesis to occur, and the temperature at which the organ is kept may also be optimized for photosynthesis.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 2B Demonstration of 24 fold increase in oxygen tension after ischemia at 10 and 20 minutes following injection of SE. FIG. 2C Illustration of significantly increased myocardial oxygen tension as a percent of baseline in the SE group.

FIGS. 4A-4F. Long-term protective and functional benefit of photosynthetic therapy. Animals underwent myocardial ischemia-reperfusion injury and were randomized to saline control (n=7) or SE therapy (n=10). a, Serum troponin at 24 hours following injury was substantially reduced in the SE group, indicating ameliorated myocardial injury. b, LV ejection fraction was increased in the SE group determined by cardiac MRI. c, End systolic volume was decreased in the SE treated animals, illustrating reduced pathologic remodeling. d, Representative 4-chamber cardiac MRI images. e,f, SE therapy resulted in a greater slope of the LV pressure-volume relationship during inferior vena cava occlusion, indicating enhanced ventricular contractility. (*=statistical significance)

FIGS. 5A-5D. SE therapy does not elicit a pathologic immune response nor persist in tissue long-term. a, Flow cytometry of blood at 0, 16, 40, and 88 hours following intravenous administration of saline or SE demonstrating no difference in CD8 T-cell and CD19 B-cell frequencies. b, No difference in peripheral CD4 T-cell frequencies at 0, 1, 2, and 7 days. c, Representative hematoxylin and eosin stained heart section revealing no abscess at 4 weeks post-therapy. d, Immunohistochemistry of heart sections at 4 weeks illustrating no evidence of retained SE.

DETAILED DESCRIPTION OF THE EMBODIMENTS

Figure 1:
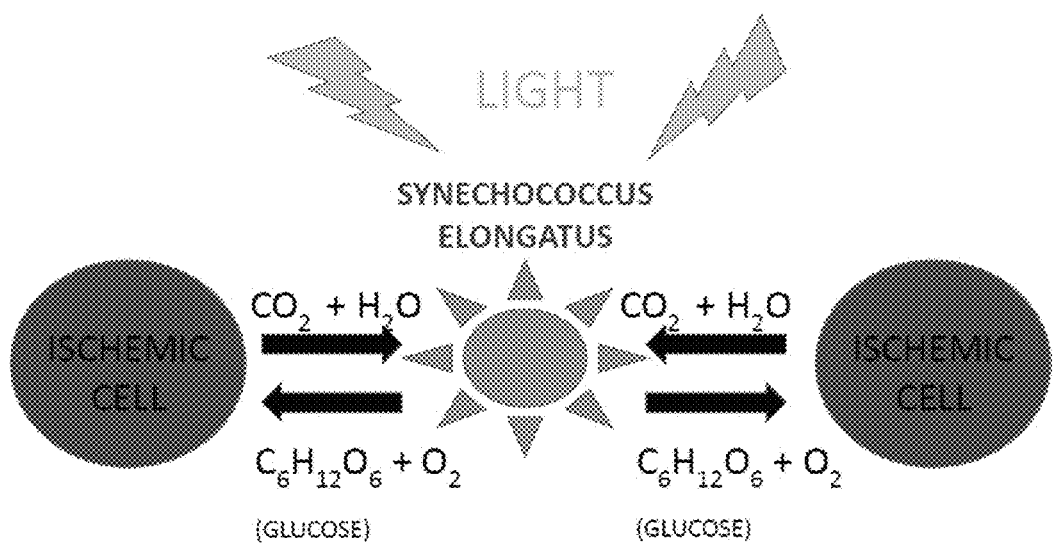
FIG. 1 Schematic of the symbiotic photosynthetic relationship between SE and ischemic cardiomyocytes enabling oxygen and glucose delivery.

The disclosed embodiments provide methods for exploiting the ability of photosynthetic microorganisms to regulate metabolic imbalances resulting from ischemia. Ischemic tissues produce undesirable $CO_2$ and reactive oxygen species. By introducing a suitable supply of photosynthetic reactions, $O_2$ is produced and $CO_2$ decreased.

Photosynthetic microorganisms. Microorganisms of interest for use in the methods of the invention are capable of photosynthesis, usually single-celled organisms, and usually bacterial organisms. The organisms may may naturally occurring or genetically engineered to enhance properties of interest.

In embodiments, the photosynthetic microorganism of the invention is cyanobacterial organism, e.g. selected from the group consisting of *Gloeobacteria; Nostocales*, e.g. *Nostocaceae, Rivulariaceae, Scytonemataceae*, etc.; *Oscillatoriophycideae*, e.g. *Chroococcales, Oscillatoriales*, etc.; *Pleurocapsales*, e.g. *Chroococcidiopsis, Chroococcopsis, Dermocarpa, Dermocarpella, Hyella, Myxosarcina, Pleurocapsa, Solentia, Stanieria, Xenococcus*, etc.; *Prochlorales* (prochlorophytes), e.g. *Prochloraceae, Prochlorococcaceae, Prochlorotrichaceae*, etc.; *Stigonematales, Capsosira, Chlorogloeopsis, Fischerella, Hapalosiphon, Iphinoe, Loriellopsis, Mastigocladopsis, Mastigocladus, Mastigocoleus, Nostochopsis, Stigonema, Symphyonema, Symphyonemopsis, Westiella, Westiellopsis*, etc.

In some embodiments the photosynthetic organism is a *Synechococcus* species, e.g. *Candidatus Synechococcus calcipolaris, Candidatus Synechococcus spongiarum, Synechococcus bigranulatus, Synechococcus elongatus, Synechococcus leopoliensis, Synechococcus lividus, Synechococcus nidulans, Synechococcus rhodobaktron, Synechococcus rubescens*, etc.

Selection of the organism may include evaluation of photosynthetic levels; wave length absorbed by chlorophyll present in the microorganism, immunogenicity and toxicity of the microorganism; growth rate of the microorganism; antibiotic sensitivity of the microorganism; pH and temperature optima; and the like. The features of interest may be present, or the microorganism may be genetically engineered to enhance a property of interest. The optimization can include both up-regulation and down-regulation of particular genes.

The term "recombinant host cell" or "engineered host cell" (or simply "host cell" or "host") refers to a cell into which a recombinant polynucleotide has been introduced. Recombinant polynucleotides can be used to transform a variety of hosts to produce a carbon-based product of interest. The host must be "competent to express," such that it provides a sufficient cellular environment for expression of endogenous and/or exogenous polynucleotides. A recombinant host cell may be an isolated cell or cell line grown in culture or may be a cell which resides in a living tissue or organism.

In various embodiments, polynucleotides encoding enzymes are introduced into the host cell such that expression of the enzyme by the host under certain conditions results in increased production of a product of interest. Examples of engineering of interest includes increased photosynthesis in a temperature range of interest; increased glucose export; increased sensitivity to an antibiotic; introduction of a conditionally expressed lethal gene as a "kill switch" for the microorganism; decreased expression of lipopolysaccharides on the cell surface; etc.

Genetic engineering of the microorganism may be effected by transformation of the host cells. A recombinant expression construct for transformation of a host cell and subsequent integration of the gene(s) of interest can be prepared by first isolating the constituent polynucleotide sequences. In some embodiments, the gene(s) of interest are homologously integrated into the host cell genome. In other embodiments, the genes are non-homologously integrated into the host cell genome. Generally, constructs containing polynucleotides are introduced into the host cell using a standard protocol, such as the one set out in Golden et al. (1987) "Genetic engineering of the Cyanobacteria chromosome" Methods Enzymol 153: 215-231 and in S. S. Golden and L. A. Sherman, J. Bacteriol. 158:36 (1984), incorporated herein by reference. The particular procedure used to introduce the genetic material into the host cell for expression is not particularly critical. Any of the well-known procedures for introducing heterologous polynucleotide sequences into host cells can be used. In certain embodiments, only a single copy of the heterologous polynucleotide is introduced. In other embodiments, more than a single copy, such as two copies, three copies or more than three copies of the heterologous polynucleotide is introduced. As is understood by the skilled artisan, multiple copies of heterologous polynucleotides may be on a single construct or on more than one construct. Polynucleotides can be operably connected to a promoter in the construct. In one embodiment, the promoter is a native *Anabaena* or *Synechococcus* promoter. For example, the promoter may be an *Anabaena* Pnir promoter.

One example of such a broadly replicative plasmid is RSF1010 (also called R300B and R1162), which is a small (8,684 bp; Scholz et al. (1989) Gene 75, 271-288) multicopy plasmid that can replicate in most Gram-negative bacteria, including cyanobacteria (Gormley and Davis (1991) *J. Bacteriol.* 173, 6705-6708). The replication of RSF1010 DNA in *Escherichia coli* utilizes three plasmid-encoded proteins, the products of replicative genes repA, repB', and repC (Scherzinger et al. (1991) *Nucleic Acids Res.* 19, 1203-1211). In addition, the minimal origin sequence required to support RSF1010 replication has been identified (Scherzinger et al. (1984) *Proc. Natl. Acad. Sci. U. S. A.* 81, 654-658). This 396-bp sequence (oriV) can be divided into two functional domains. The first domain is made up of three direct repeats of 20 by and adjacent GC-rich and AT-rich segments of DNA. The iterons are the primary binding site for the plasmid-encoded initiator protein RepC. In addition, RepC promotes localized melting of the AT-rich oriV segment. The second domain contains two oppositely oriented sites for the initiation of DNA synthesis, termed ssiA and ssiB. These sequences, which are on the plasmid I- (upper) and r- (bottom) strand, respectively, can function in a single-stranded form as a template for the synthesis of a unique DNA or mixed RNA/DNA primer by the RepB' protein, and they are the primary positions for the initiation of each plasmid strand. Although both of the ssi signals of RSF1010 are required for normal plasmid replication, they can be replaced by other types of priming signals such as the primosome assembly site from phage ϕX 174 or the priming signal from phage G4. When both ssi sites are replaced by heterologous priming signals, the function of the chimeric oriV is no longer dependent on RepB' but is still dependent on RepA and RepC. RepB is the full-length product of the repB gene, whereas RepB' results from an in-frame start of translation.

A gene of interest can be transiently introduced into the host cell through use of a plasmid or shuttle vector. In other embodiments, the gene of interest is permanently introduced into the chromosome of the host cell. Chromosomal integration techniques are known to the skilled artisan and have been described in, for example, Zhou and Wolk, 2002 J. Bacteriol., 184(9):2529-2532. Briefly, the gene of interest is fused to a promoter and then subcloned into an integration vector. This construct is introduced into the host cell for double homologous recombination at specific loci on the host cell chromosome. In many embodiments, homologous recombination takes place at two loci of the host cell chromosome. The recombinant cells can be selected by monitoring loss of a conditional lethal gene, such as sacB. Further diagnostic verification by the polymerase chain reaction can be performed. In many embodiments, the gene of interest will be inserted into the chromosome at the site of a gene that is desired to be deleted or inactivated.

In some embodiments, strain engineering techniques such as directed evolution and acclimation can be used to improve the performance of photosynthetic cells at pH, temperature, iconicity, etc. conditions of interest. Strain engineering is known in the art. As cells generally possess complex regulatory systems for traits such as product tolerance, productivity, and yield, directed evolution and screening can be used to create global genome-wide alterations needed to develop strains with desired characteristics. Certain embodiments will use directed evolution under fluctuating temperature, pH, and $CO_2/O_2$ levels to generate stable, heritable genetic improvements in productivity, yield, and robustness to conditions useful in the methods.

The photosynthetic cells are provided in a dose that is effective in correcting metabolic imbalances that happen in mammalian cells during ischemic conditions. The concentration of the photosynthetic cells in an ex vivo suspension may be up to about $10^2$/ml, up to about $10^3$/ml, up to about $10^4$/ml, up to about $10^5$/ml, up to about $10^6$/ml, up to about $10^7$/ml, up to about up to about $10^8$/ml, up to about $10^9$/ml, up to about $10^{10}$/ml. Where the photosynthetic organism is provided in a device for localized treatment, the concentrations within the device may be higher, e.g. up to about $10^6$/ml, up to about $10^7$/ml, up to about up to about $10^8$/ml, up to about $10^9$/ml, up to about $10^{10}$/ml, up to about $10^{11}$/ml, up to about $10^{12}$/ml, up to about $10^{13}$/ml, up to about $10^{14}$/ml. Where the photosynthetic microorganism is systemically administered, the dose can vary with the size of the organism, but typically the blood concentration will be not more than about $10^5$/ml, not more than about $10^4$/ml, not more than about $10^3$/ml, not more than about $10^2$/ml.

The effective dose is that dose that increases $O_2$ present in the tissue, relative to the concentration of $O_2$ present in the absence of treatment. The increase, e.g. after about 5 minutes, after about 10 minutes, after about 15 minutes, after about 20 minutes, after about 30 minutes, after about 45 minutes, after about 1 hour, after about 2 hours, after about 3 hours, or more; may be an increase of at least about 5%, at least about 10%, at least about 15%, at least about 20%, at least about 25%, at least about 30%, at least about 40%, at least about 50%, at least about 75%, at least about 85%, at least about 95% or more.

Light Source. In order for photosynthesis to occur, light must be present. Various light sources are contemplated for use in the methods of the invention. Preferred light sources provide light in a range that is well-absorbed by the chlorophyll present in the microorganism, i.e. a light source having one or more emission wavelengths or wavebands substantially equal to an absorbing wavelength or waveband; and generate little or no heat. In certain situations, e.g. ex vivo treatment of organs, open surgery, and the like, ambient light provided by lamps, etc. are sufficient. However, in many situations it will be desirable to provide a light source that can be placed or implanted in close proximity to the photosynthetic microorganisms.

For example, optical fibers in a hand-held probe can be used to deliver light to the surgically exposed treatment site from a remote source, e.g. lasers, diode arrays, etc. coupled to optic fibers. A light source can be positioned with a catheter having a distal end and a proximal end; the light source is disposed at the distal end of the catheter. The catheter and the source of light are moved into a patient's body, and the catheter is positioned so that its distal end and the light source are disposed proximate to the internal, in vivo treatment site. The catheter may include at least one lumen that extends generally between the proximal and distal ends of the catheter.

In another embodiment, the light source is invasively disposed proximate to the internal, in vivo treatment site inside a patient's body, and left until the desired therapeutic change has occurred. Invasively disposing the source within the patient's body can include leaving the light source implanted within the patient's body while the therapeutic treatment is performed.

Light sources of interest include LED and solid-state laser diode (LD). LEDs have a relatively broad emission pattern wherein about one-half of the light is emitted through the side walls and the remainder through the top of the LED. As a result, it is difficult to concentrate all of the emitted light and direct it into the end of an adjacent optical fiber to deliver the light from an external source to an implantable probe at the treatment site. Typically, assuming a Lambertian LED emission pattern, an optical fiber may collect only about 36% of the emitted light. By comparison, virtually all of the light emitted by LEDs in an implantable probe are available to activate photosynthesis at the treatment site. A power supply for the light source can be integrated into the source, or can be an external power supply and electrical conductors that are connected to the power supply. Transcutaneous charging technology could also be utilized.

Device. An implantable photosynthetic device can be used to target an organ of interest, to concentrate the photosynthetic microorganisms, to shield the photosynthetic microorganisms from the recipient immune system and provide an easy removal of the photosynthetic microorganisms after a procedure. The device allows passage of small molecules across a membrane, but contains and protects the bacteria. A device is placed or implanted in fluid communication with the targeted tissue, and can optionally be adapted to be spliced in line with a blood vessel, so that blood flows freely through the device. The device typically contains a biomass cartridge, containing an effective dose of the photosynthetic microorganisms. The desired organisms are contained within a semipermeable membrane capsule. In order to maximize the surface area for delivery of the drug maximizing the diffusion rate of the product into the blood stream it may be desirable to encapsulate colonies of the microorganisms within smaller membrane units within the membrane capsule. These smaller membrane units may take the form of microspheres. The semipermeable membrane capsule surrounds the microspheres and allows for passage of $CO_2$ into the capsule and the passage of photosynthetically produced $O_2$ out of the capsule. The semi-permeable membrane may be constructed of materials known to the art. The device is preferably configured of a biocompatible, nonthrombogenic plastic such as polyurethane or Teflon®.

Preservation Solutions. For ex vivo embodiments, the photosynthetic microrganisms can be provided in the context of a preservation solution known in the art for organ maintenance. Such solutions can be optimized to increase photosynthesis. Various flush solutions are used for organ preservation and protection during cardiac surgery. Each substantially differs in their composition, but the purposes of each are similar: to prevent cellular edema, to delay cell destruction, and to maximize organ function after perfusion is reestablished.

Euro-Collins solution contains high concentrations of potassium (110 mM), phosphate (60 mM), and glucose (180 mM). The solution is adequate for use in preserving the heart, liver, and lung. Ross-Marshall citrate solutionsare alternatives to the Collins solutions. Their electrolytic compositions are similar except that citrate replaces phosphate, and mannitol replaces glucose. The citrate acts as a buffer and chelates with magnesium to form an impermeable molecule that helps stabilize the extracellular environment. Bretschneider histidine tryptophan ketoglutarate (HTK) solution was found to be effective in liver and kidney preservation. Its contents include histidine (200 mM), mannitol (30 mM), tryptophan and alpha-ketoglutaric acid. It also contains low concentrations of sodium, potassium, and magnesium. Histidine serves as a buffer, and tryptophan, histidine, and mannitol act as oxygen free-radical scavengers. The solution improved renal function after transplantation compared with Euro-Collins solution. Phosphate-buffered sucrose solution contains sucrose 140 mmol/L and sodium hydrogen and dihydrogen phosphate as buffers.

University of Wisconsin (UW) solution has been considered the standard for renal and hepatic preservation, effectively extending the ischemic time for kidneys and livers and allowing them to be transported considerable distances to waiting recipients. UW solution has also been successfully applied to small-bowel and heart preservation. The composition of the solution is complex. Analysis of its various components has shown that some may be omitted or replaced with results similar to that of the original solution. The solution has an osmolality of 320 mmol/kg and pH 7.4 at room temperature and is composed of the following: Potassium 135 mmol/L, Sodium 35 mmol/L, Magnesium 5 mmol/L, Lactobionate 100 mmol/L, Phosphate 25 mmol/L, Sulphate 5 mmol/L, Raffinose 30 mmol/L, Adenosine 5 mmol/L, Allopurinol 1 mmol/L, Glutathione 3 mmol/L, Insulin 100 U/L, Dexamethasone 8 mg/L, optionally Hydroxyethyl starch (HES) 50 g/L, Bactrim 0.5 ml/L.

Celsior is a recently developed extracellular-type, low-viscosity (due to the absence of HES) preservation solution that couples the impermeant, inert osmotic carrier from UW solution (by using lactobionate and mannitol) and the strong buffer from Bretschneider HTK solution (by using histidine). The solution was specifically designed for heart transplantation. It is being currently used in clinical lung, liver, and kidney transplantations. The solution includes Sodium 100 mmol/L, Potassium 15 mmol/L, Magnesium 13 mmol/L, Calcium 0.25 mmol/L, Lactobionate 80 mmol/L, lutathione 3 mmol/L, Glutamate 20 mmol/L, Mannitol 60 mmol/L, Histidine 30 mmol/L.

ET Kyoto solution is also being actively investigated in clinical trials for transplantation of the lungs, heart, and other organs. Its constituents include the following: Sodium 100 mmol/L, Potassium 44 mmol/L, Phosphate 25 mmol/L, Trehalose 41 mmol/L, HES 30 gm/L,luconate 100 mmol/L.

Conventionally organs are maintained in a hypothermic state, e.g. rapidly cooled to approximately 4° C. by flushing out the vascular system with an appropriate organ-preservation solution. In the methods of the invention it can be desirable to increase the temperature in order to provide for a balance between ischemia and photosynthesis, e.g. at around about 10° C., at around about 15° C., at around about 20° C., at around about 25° C., at around about 30° C.

Methods of Use. In various embodiments, methods are provided for reducing the adverse effects of ischemia on a mammalian, e.g. a human, individual. In such methods, an effective dose of a photosynthetic microorganism is brought into fluid communication with the tissue or organ that is ischemic, or at risk of ischemia. Frequently, an organ at risk of ischemia is involved in a surgical procedure, an organ transplant, and the like. In such methods, the effective dose of photosynthetic microorganisms can be provided preceeding the surgical procedure, or concurrently with the surgical procedure. The organisms may be removed following the procedure, e.g. by administering an activator of a "kill-switch" engineered into the microorganism; by administering an effective dose of an antibiotic that the microorganism is sensitive to, or by removal of a device comprising the photosynthetic microorganisms.

Surgical procedures, as used herein, may also refer to the stabilization and maintenance of organs, including solid organs, prior to a transplantation procedure. As is known in the art, solid organs may be transplanted from a donor to a recipient such that the organ is placed into the appropriate position in the recipient body. In some cases, the cardiovascular connections between the solid organ may be physiologically integrated into the recipient body. In some cases, the organ may be from a living donor. In other cases, the organ may be from a deceased donor. In some cases, the solid organ may be HLA-matched between the donor and the recipient. In other cases, the solid organ may be HLA-mismatched between the donor and the recipient.

Any solid organ that may be used for organ transplantation may be used with the methods described herein. In some cases, the organ may be a kidney, lung, pancreas, pancreatic islet cells, heart, intestine, colon, liver, skin, muscle, gum, eye, tooth and the like as known to those of skill in the art. In some cases, the organ may be a complete organ. In other cases, the organ may be a portion of an organ. In other cases, the organ may be cells from a tissue of an organ.

Using the methods described herein, the solid organ is harvested and transplanted in accordance with conventional practice. During the period of time when the organ is being stored and transported, the organ may be perfused with a preservation solution, as described above, in which an effective dose of photosynthetic organisms has been suspended. In other embodiments, a device comprising an effective dose pf photosynthetic organisms is placed in fluid communication with the preservation solution, in order to correct the metabolic imbalances that result from an ischemic condition.

The photosynthetic microorganisms can be present for a desired peior of time, in order to effect the desired correction of metabolic imbalance. The period of time may be up to about 10 minutes, up to about 20 minutes, up to about 30 minutes, up to about 45 minutes, up to about 60 minutes, up to about 90 minutes, up to about 2 hours, up to about 3 hours, up to about 5 hours, up to about 6 hours, up to about 8 hours up to about 12 hours, up to about 18 hours, up to about 1 day, up to about 2 days, or more.

Also provided are reagents and kits thereof for practicing one or more of the above-described methods. The subject reagents and kits thereof may vary greatly. Reagents of interest include reagents, for example, preservation solutions for organ transplantation, which are optionally optimized for maintenance of the microorganisms and for photosynthesis. Reagents may also comprise antibiotics and other reagents for killing the microorganisms at the conclusion of the procedure. Reagents may also comprise agents to mask or downregulate LPS on the microorgansisms.

Generally a kit or device will also include an effective dose of a photosynthetic organism, including a genetically engineered organism as described herein. The organism may be suspended, frozen, provided in a biomass catridge for use in a device, and the like.

Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such kits may also include instructions to access a database. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

It is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

The following examples are offered by way of illustration and not by way of limitation.

EXPERIMENTAL

Example 1

Creation of a Novel Endosymbiotic System for Photon Powered Myocardium in the Ischemic Heart Current strategies for managing myocardial ischemia are sometimes unable to sufficiently restore myocardial energetics and ventricular function. This study's goal was to develop a completely novel method of enhancing bioenergetics in the setting of myocardial ischemia by implementing a photosynthetic system. Targeted delivery of a photosynthetic agent to a region of myocardial ischemia enables light to fuel cardiomyocytes and local oxygen production to enhance ventricular function.

Male Wistar rats at 10 weeks old were utilized for the ischemia model. The rats were anesthetized, intubated, and underwent sternotomy followed by placement of an LV catheter and aortic flow probe. Baseline intramyocardial $O_2$ tension was assessed along with myocardial metabolic activity via thermal imaging. The LAD was then ligated 2 mm below the left atrial appendage, and after 10 minutes animals were randomized (n=5/group) to receive saline injection or $5 \times 10^6$ photosynthetic Synechococcus elongatus (SE) directly to the ischemic myocardium (IM). Hemodynamic, $O_2$, and thermal data were collected at multiple time points with consistent photon exposure.

Baseline intramyocardial $O_2$ assessment revealed no difference between groups. At 10 minutes after injection, the treatment group demonstrated augmented oxygenation as a percentage of baseline in the IM compared to control (37.5±8.0% vs. 10.8±2.1%; p=0.01). Ultra-sensitive thermal imaging of the IM at 20 minutes post-injection, revealed significantly elevated myocardial temperature as a percent of baseline in SE compared to control (98.1±1.0% vs. 95.5±0.4%; p=0.04). Hemodynamic assessment at 45 minutes post-injection demonstrated enhanced max dP/dt (5344±542 mmHg/s vs. 2912±258 mmHg/s; p<0.01) and cardiac output. (26±2 mL/min vs. 17±3 mL/min; p=0.04) in SE compared to control. Immunologic and infectious analysis demonstrated no significant inflammatory response or infection to SE treatment.

Targeted intramyocardial delivery of a photosynthetic agent to ischemic territory enables localized oxygen production, enhanced metabolic activity, and augmented ventricular function in a rat model of acute myocardial ischemia. This strategy of utilizing light as a fuel source for myocardium represents a completely novel approach to the treatment of cardiac ischemia.

Synechococcus elongatus (SE) is a naturally occurring blue-green algae that photosynthesizes at broad wavelengths. It has traditionally been studied for elucidating circadian rhythms[11] and, more recently, for the enhanced production of biofuels utilizing $CO_2$. Additionally, SE is easily genetically engineered to manipulate its metabolic activity and production of $O_2$ and glucose. Based on these abilities, this study aimed to utilize SE as a symbiotic partner to ischemic cardiomyocytes in vivo in order to clear $CO_2$ and provide these cells with the essential $O_2$ and glucose required for metabolic activity when blood flow is absent. In essence, the SE serves to balance a traditionally imbalanced equation in an ischemic milieu involving $CO_2$, $O_2$, $H_2O$, and glucose (FIG. 1). This allows light to become a fuel source for cardiomyocytes, while potentially obviating the need for revascularization and restoration of perfusion.

The objectives of this work were to successfully isolate SE, locally target them to ischemic myocardium, and demonstrate enhanced $O_2$ tension, and ventricular function once the symbiotic relationship was established. Additionally, we aimed to study the in vivo immune response to this therapy. This novel photosynthetic strategy opens unexplored avenues of treating patients with ischemic disease.

This study demonstrated the first successful utilization of a photosynthetic system as a means of correcting tissue ischemia. The data show that SE can be easily and safely isolated allowing for direct delivery to ischemic myocardium. This resulted in augmented tissue oxygenation, increased myocardial surface temperature likely secondary to metabolic activity, and greatly enhanced LV function in an ischemic setting. Immunologic analysis demonstrated no obvious inflammatory response to the therapy. The minimal response appeared to be less significant than that of receiving a plasma transfusion. Importantly, all blood cultures remained negative for a week even when $5 \times 10^8$ SE cells were delivered intravenously, and the animal showed no clinical signs of infection.

The finding of elevated increased tissue oxygenation is a critical one as it forms the basis for enhanced myocardial bioenergetics. By allowing aerobic respiration to occur, ATP production is greatly enhanced while lactic acid release is mitigated with the decrease in anaerobic glycolysis. Clinically, this principle is utilized universally as providers strive to revascularize ischemic myocardium as quickly as possible in the setting of a ST elevation myocardial infarction. In this model, by quickly restoring oxygenation following an acute LAD occlusion, the heart demonstrated increased metabolic activity and improved ventricular function. Importantly, thermal imaging has been described as an effective and accurate method of inferring metabolic activity. Overall, the chronology of the data points suggests that introduction of the photosynthetic SE leads to increased myocardial cellular respiration 10 minutes following therapy, driving enhanced metabolism and bioenergetics at 20 minutes, and ultimately resulting in augmented LV function at 45 minutes.

While the benefits of this strategy to address tissue ischemia are appealing, a critical and obvious question centers on the immune response to SE. This study addresses this question by implementing flow cytometry to examine markers of inflammation at serial time-points following systemic exposure to SE. It is important to note that the therapeutic strategy employs a targeted delivery; therefore, the intravenous administration is an extreme scenario. The data showed that there was no dramatic inflammatory response in rats that received a plasma transfusion or SE. Specifically, there was no increase in TNF$\alpha$, a known marker of sepsis. A critical point is that SE do not possess the type of LPS seen in virulent gram negative bacteria clinically. A significant limitation here is that only one animal was used per group for this preliminary experiment. Additional formal immunologic studies will be statistically evaluated.

This model of myocardial ischemia allowed the chest to be open through the study enabling light to easily reach the ischemic myocardium. This is possible in some clinical scenarios, such as myocardial protection during cardiac surgery; however, most clinical situations do not allow for external light to reach ischemic tissue. Engineering miniature and durable light sources that penetrate the targeted tissue is of interest for alternative therapies. Evaluation also includes magnetic resonance spectroscopy and myocardial tissue analysis to assess energetics.

Example 2

A Novel Endosymbiotic System for Photon Powered Myocardium in the Ischemic Heart Cardiovascular disease is the leading cause of death globally and accounts for almost $1 trillion in costs. Over the past decades, research and innovation have enabled advances in preventative, pharmacologic, and surgical strategies to greatly augment the clinician's ability to treat once devastating cardiac events. Stemming from these accomplishments, a wave of exploration into cardiac tissue regeneration and angiogenesis has yielded exciting results in preclinical models and early clinical trials. While these myocardial repair strategies possess great popularity, it remains critical to pioneer alternative and uncharted pathways for the treatment of myocardial injury. This study provides a novel method of correcting myocardial ischemia by implementing a symbiotic photosynthetic system where light, rather than blood, fuels cardiomyocytes. Here we show that delivery of *Synechococcus elongatus*, a photosynthetic cyanobacteria, to the ischemic heart greatly augments cardiac performance. Specifically, we found that photosynthetic therapy increases tissue oxygenation by 24.6%, preserves myocardial metabolism, and enhances cardiac output by 59.4%. Furthermore, this approach is non-toxic and does not elicit a robust immune response. These results provide an novel strategy in coupling symbiosis and photosynthesis to treat tissue ischemia, forming the foundation of a new generation of medical therapeutics.

*Synechococcus elongatus* (SE) is a naturally occurring blue-green algae that photosynthesizes at broad wavelengths. It has been studied for elucidating circadian rhythms and, more recently, for the enhanced production of biofuels utilizing $CO_2$. Additionally, SE is easily genetically engineered to manipulate its metabolic activity and production of $O_2$ and glucose. Based on these abilities, this study hypothesized that SE could be utilized as a symbiotic partner to ischemic cardiomyocytes in vivo to clear $CO_2$ and provide these cells with the essential $O_2$ and glucose required for metabolic activity when blood flow is absent. In essence, the SE serves to balance a traditionally imbalanced equation in an ischemic milieu involving $CO_2$, $O_2$, $H_2O$, and glucose. This allows light to become a fuel source for cardiomyocytes, while potentially obviating the need for revascularization and restoration of perfusion.

Figure 2A:
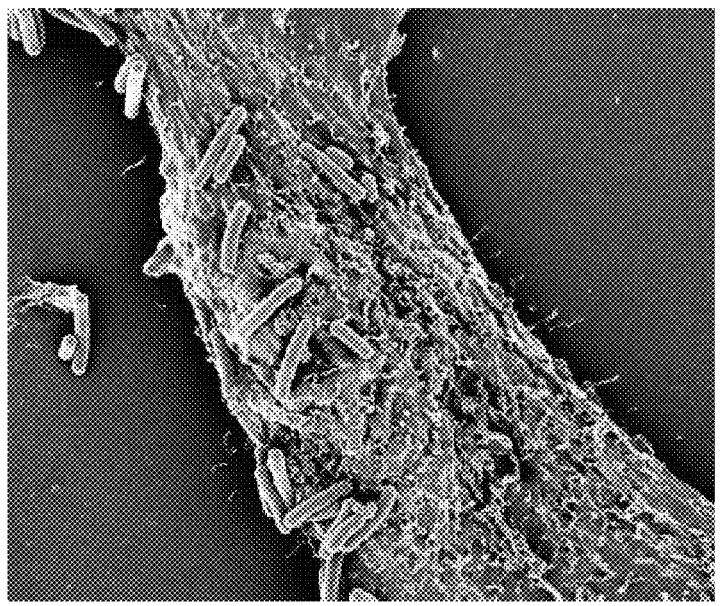
FIGS. 2A-2B. Flow probe on ascending aorta SE successfully co-cultured with rat cardiomyocytes and application to an in-vivo model. a, Scanning electron microscopy of multiple SE cyanobacteria with a single rat cardiomyocyte. b, In vivo model of myocardial ischemia with suture occlusion of left anterior descending coronary artery and flow probe placement around the ascending aorta. Line graph demonstrating increased oxygen production over time following injection in SE treated group (asterisk denotes sig).
Figure 2B:
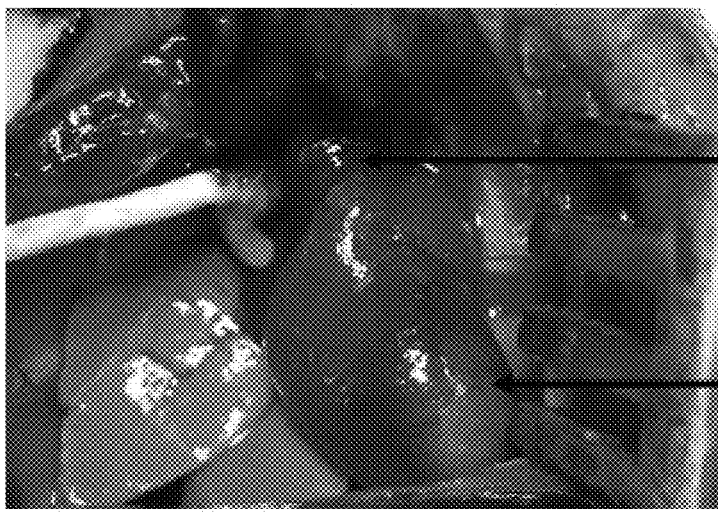

To test this hypothesis, we isolated SE and co-cultured them with isolated rat cardiomyocytes (FIG. 2a). Importantly, the SE did not affect the cardiomyocyte survival in standard conditions in vitro. We then generated an in vivo model of myocardial ischemia whereby Wistar rats were sedated and intubated, underwent sternotomy with occlusion of the left anterior descending coronary artery (LAD), and had a pressure-volume catheter introduced into the left ventricle (LV) via the carotid artery for precise hemodynamic assessment along with a flow probe around the ascending aorta for cardiac output measurement (FIG. 2b). The chest remained open to provide a standard light source.

Figure 3A:
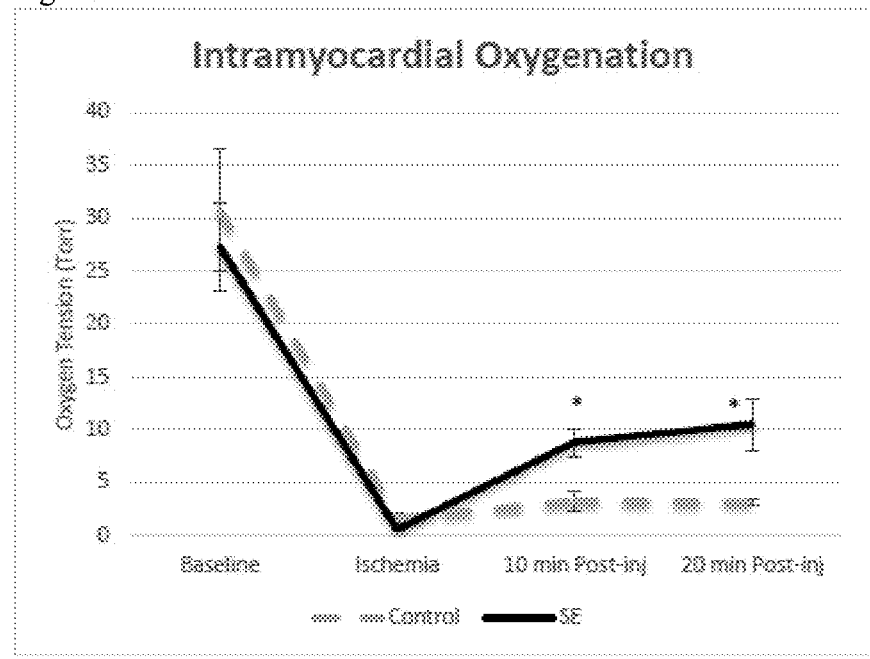
FIGS. 3A-3C. Enhancement of oxygenation, metabolism, and cardiac function in acute ischemia. Animals were randomized to receive saline control (n=5) or SE therapy (n=5). a, Phosphorescent probe technology was used to quantify tissue oxygenation at baseline, time of ischemia, 10 and 20 minutes post-therapy. The SE treated group showed significantly elevated levels of tissue oxygenation at 10 and 20 minutes with an almost 25 fold increase relative to the time of ischemia. b, Thermal imaging was employed to quantify epicardial surface temperature as a measure of myocardial energetics. SE treated animals demonstrated significantly increased surface temperature at 20 minutes post-therapy with a positive trajectory. Representative thermal images are provided. c, Pressure-volume and flow probe assessment revealed significantly enhanced maximum LV pressure, dP/dt, and cardiac output at 45 minutes post-therapy. (*=statistical significance)
Figure 3A:
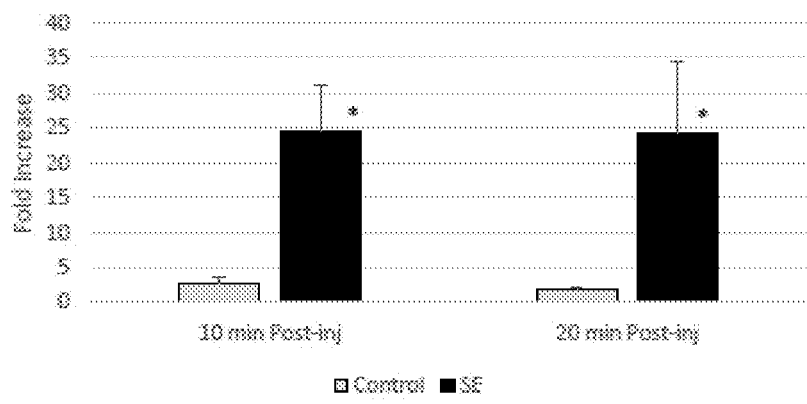

Our first objective in the in vivo model was to quantify myocardial oxygen tension at multiple time-points. Critically, the technique of utilizing a phosphorescent probe enabled us to directly measure tissue oxygenation while avoiding off-target scatter from ventricular blood. Oxygen tension was quantified at baseline and 10 minutes following LAD occlusion with initiation of ischemia. At this point, animals were randomized to receive direct intramyocardial SE injection or saline alone. Oxygen tension was then reassessed at 10 and 20 minutes. We found that baseline oxygen levels were similar between groups at 30 torr and predictably dropped to near-zero in the ischemic myocardium. Interestingly, the SE treated hearts demonstrated a nearly 25 fold increase in oxygenation levels from the nadir of ischemia. The saline treated group, by comparison, showed a less than 3 fold increase in oxygen tension (FIG. 3a). The finding of elevated tissue oxygenation is a critical one as it forms the basis for enhanced myocardial bioenergetics (Table 1).

TABLE 1

Myocardial Oxygenation

|  | Baseline $O_2$ (torr) | 10 Min $O_2$ (torr) | 20 Min $O_2$ (torr) | 10 Min $O_2$: Infarct $O_2$ | 20 Min $O_2$: Infarct $O_2$ |
|---|---|---|---|---|---|
| Control | 30.7 ± 5.7 | 3.2 ± 1.0 | 3.1 ± 0.3 | 2.7 ± 0.9 | 1.8 ± 0.5 |
| SE | 27.3 ± 4.1 | 8.8 ± 1.3 | 10.5 ± 5.1 | 24.6 ± 6.4 | 24.4 ± 10.2 |
| p-value | 0.3 | <0.01 | 0.01 | <0.01 | 0.03 |

Figure 3B:
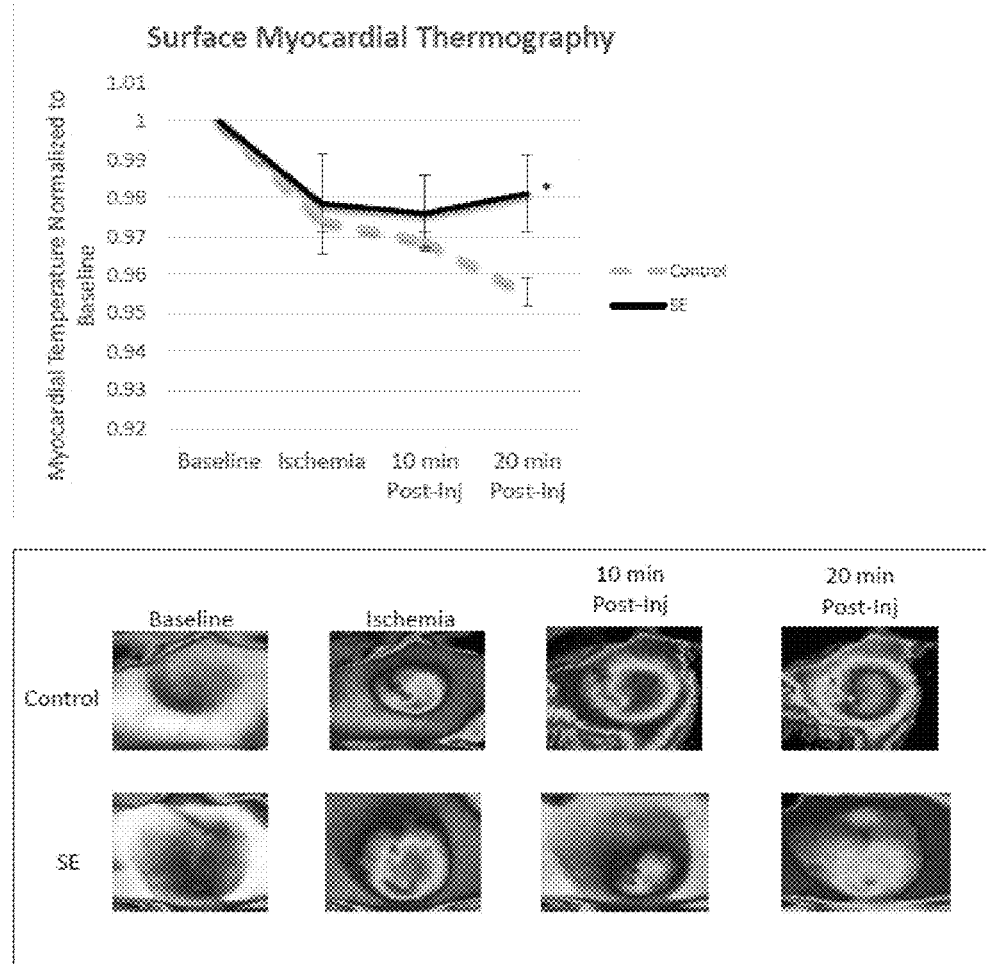

We next turned our attention to evaluating the myocardial metabolic state in vivo. This was accomplished utilizing FLIR® thermal imaging videography. There was no difference in baseline LV surface temperature, and both groups showed a similar relative decrease in temperature, as a ratio to baseline, in the ischemic region following LAD ligation. At 10 minutes following injection there remained no significant difference between groups; however, at 20 minutes the SE group demonstrated a significantly enhanced preservation of surface temperature in the ischemic region (FIG. 3b). Representative thermal images at these four time-points are provided. Importantly, the control group showed a steady decrease in ischemic region surface temperature over time, whereas the SE group demonstrated an increase in local temperature from the time of ligation (Table 2). As previously published, thermal imaging is an effective method of quantifying in vivo metabolic activity.

TABLE 2

Myocardial Surface Temperature

|  | Baseline (° F.) | Infarct Temperature Normalized to Baseline | 10 Min Temperature Normalized to Baseline | 20 Min Temperature Normalized to Baseline |
|---|---|---|---|---|
| Control | 94.67 ± 1.13 | 0.974 ± 0.003 | 0.969 ± 0.002 | 0.956 ± 0.004 |
| SE | 94.78 ± 1.02 | 0.979 ± 0.012 | 0.976 ± 0.009 | 0.981 ± 0.01 |
| p-value | >0.5 | >0.5 | 0.29 | 0.04 |

Figure 3C:
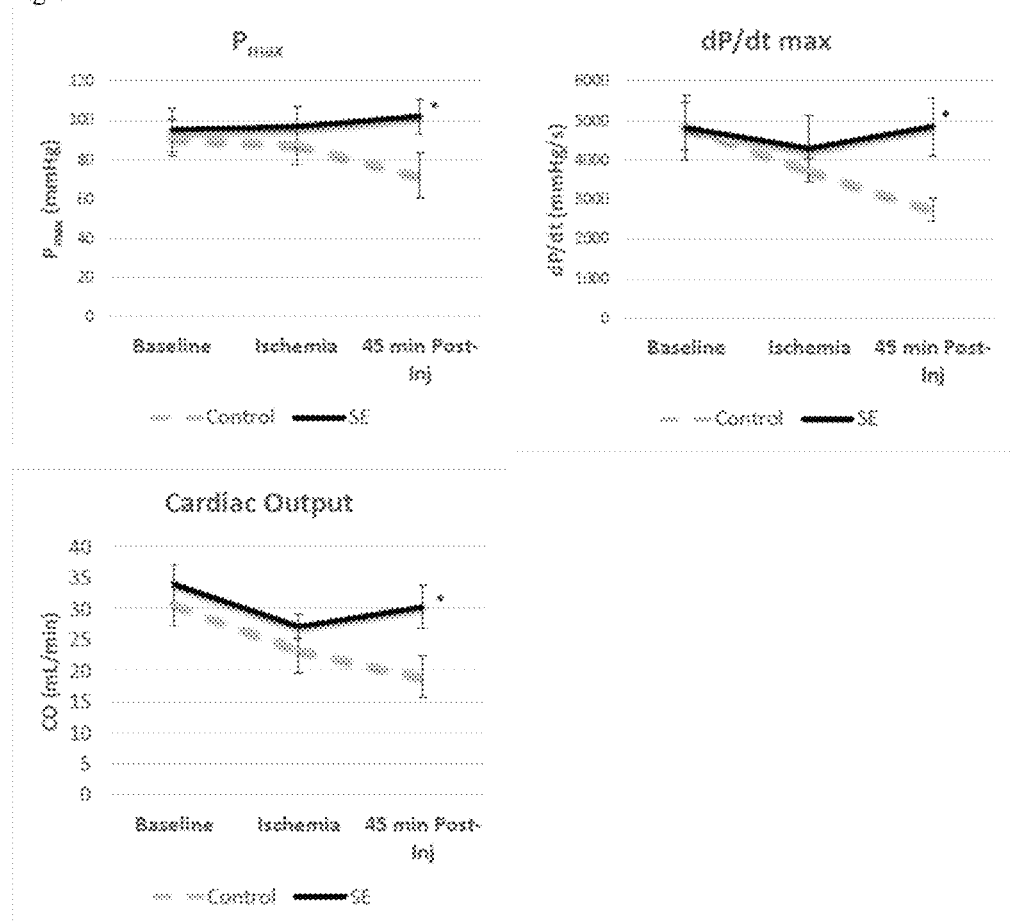

As our data at this point suggested an enhancement in tissue oxygenation leading to an upregulated myocardial metabolic state, we sought to explore the immediate functional effects of photosynthetic therapy. This was performed utilizing the ascending aortic flow probe for cardiac output (CO) quantification and an LV pressure-volume catheter for hemodynamic assessment at baseline, post-ischemia induction, and 45 minutes following photosynthetic therapy. There was no baseline difference between control and SE groups with regard to maximum LV pressure ($P_{max}$), dP/dt, and CO. At 45 minutes post-intervention, however, the SE treated animals demonstrated augmented $P_{max}$, dP/dt, and CO (FIG. 3c), consistent with enhanced ventricular contractility and overall cardiac performance (Table 3).

TABLE 3

LV Hemodynamics

| Control | Baseline | Infarct | 45 Min |
|---|---|---|---|
| Pmax (mmHg) | 91.1 ± 9.4 | 88.0 ± 10.2 | 72.0 ± 11.5 |
| dP/dt (mmHg/sec) | 4876 ± 610 | 3749 ± 300 | 2759 ± 281 |
| Cardiac Output (mL/min) | 30.8 ± 3.4 | 23.4 ± 3.7 | 19 ± 3.4 |

| SE | Baseline | Infarct | 45 Min |
|---|---|---|---|
| Pmax (mmHg) | 95.3 ± 11.1 | 96.8 ± 10.2 | 102.2 ± 8.8 |
| dP/dt (mmHg/sec) | 4821 ± 834 | 4298 ± 827 | 4851 ± 725 |
| Cardiac Output (mL/min) | 33.4 ± 3.7 | 27.2 ± 2.4 | 30.3 ± 4.8 |
| p-value Pmax | >0.5 | >0.5 | 0.04 |
| p-value dP/dt | >0.5 | >0.5 | 0.02 |
| p-value Cardiac Output | >0.5 | 0.4 | 0.04 |

After establishing the heart's increased bioenergetic and functional state immediately following photosynthetic SE administration, we next examined the long-term effects of this therapy. To do this, we employed an ischemia-reperfusion (IR) small animal model of cardiomyopathy. Here, the Wistar rats undergo a left thoracotomy to expose the heart and enable consistent light exposure, the LAD is temporarily occluded to induce ischemia, animals are randomized to saline control or SE delivery, and the occlusion is removed to allow for reperfusion of the ventricle. The animals are recovered and evaluated over a 4-week timeframe. Biochemical analysis at 24 hours following recovery revealed that serum troponin, a clinical marker of myocardial injury and infarction, was significantly reduced in the SE treated group (FIG. 4a). This finding suggests a long-term myocardial protective effect from photosynthesis driven bioenergetics.

To determine whether reduced cardiac injury translated to enhanced functionality, we utilized cardiac MRI and LV pressure-volume catheterization at 4 weeks. Cardiac MRI analysis revealed a significantly augmented LV ejection fraction and reduced end systolic volume in SE treated animals (FIG. 4b-d), consistent with improved cardiac function and mitigated pathologic remodeling. Further supporting this finding, intraventricular catheterization demonstrated significantly improved LV contractility as determined by the end systolic pressure-volume relationship (FIG. 4f,e). Overall, these findings strongly support a long-term protective benefit of photosynthetic therapy, which translates to enhanced cardiac performance (Table 4).

TABLE 4

LV Function in the Ischemia-Reperfusion Model

|  | Troponin (ng/mL) | Ejection Fraction (%) | End Systolic Volume (μL) | Slope of End Systolic Pressure-Volume Relationship |
|---|---|---|---|---|
| Control | 16.5 ± 10.5 | 36.9 ± 4.7 | 487 ± 140 | 0.19 ± 0.08 |
| SE | 6.5 ± 4.8 | 48.3 ± 10.5 | 327 ± 133 | 0.35 ± 0.12 |
| p-value | 0.05 | 0.02 | 0.03 | 0.01 |

Figure 5B:
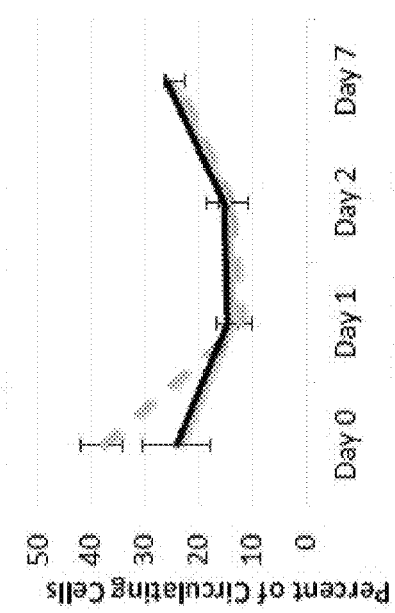
Figure 5C:
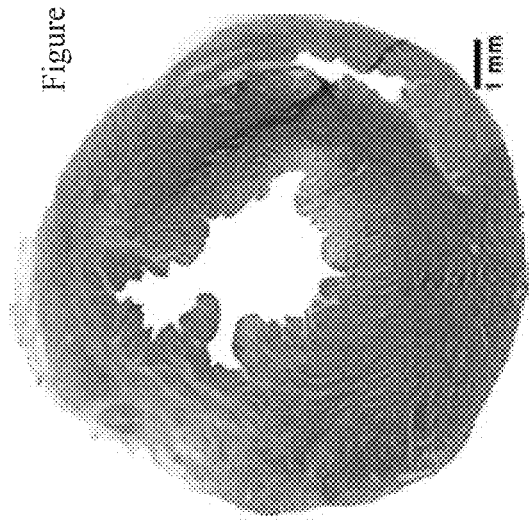
Figure 5D:

Following demonstration of the photosynthetic strategy's benefits, we aimed to evaluate the potential in vivo toxicity and immune response. Animals were randomized to receive an intravenous injection of 1 mL saline control or $5\times10^8$ SE. Blood samples were then acquired at multiple time points over a 1 week period to assess for infection and immune response. Clinically, the animals demonstrated no signs of infection. Blood cultures were also persistently negative over a 24 hour to 1 week period. Serial flow cytometry on serum was performed demonstrating no difference in the CD8 T-cell and CD19 B-cell population (FIG. 5a). There was also no difference in the circulating CD4 population (FIG. 5b). Along with evaluating the immune response, we explanted the hearts at 4 weeks to assess for abscess formation and the presence of SE. Histology and immunohistochemistry demonstrated no abscess formation nor the residual SE at 4 weeks after therapy (FIG. 5c,d). These data are consistent with SE photosynthetic therapy as being non-toxic and not eliciting a robust pathologic immune response.

This study demonstrates the first successful utilization of a photosynthetic system as a means of correcting tissue ischemia. Moreover, this strategy relies on a symbiotic relationship between a photosynthetic single celled organism and an ischemic mammalian myocyte. The SE utilize the $CO_2$ and $H_2O$ released by the oxygen depleted cell, and convert it to glucose and $O_2$ with light serving as the energy source. By balancing a pathologically unbalanced equation, cardiomyocytes are protected, translating to improved cardiac function. The data show that SE can be efficiently isolated allowing for direct delivery to ischemic myocardium. This resulted in augmented tissue oxygenation, increased myocardial surface temperature likely secondary to metabolic activity, and greatly enhanced LV function in an ischemic setting. Immunologic analysis demonstrated no obvious inflammatory response to the therapy. Importantly, all blood cultures remained negative for a week even when $5\times10^8$ SE cells were delivered intravenously, and the animal showed no clinical signs of infection.

As briefly mentioned, increased tissue oxygenation forms the basis for enhanced myocardial bioenergetics. By allowing aerobic respiration to occur, ATP production is greatly enhanced while lactic acid release is mitigated with the decrease in anaerobic glycolysis. Clinically, this principle is utilized universally as providers strive to revascularize ischemic myocardium as quickly as possible in the setting of a myocardial infarction. In this model, by quickly restoring oxygenation following an acute LAD occlusion, the heart demonstrated increased metabolic activity and improved ventricular function.

Extending from the acute ischemia model, the ischemia-reperfusion model provided significant insight to the translatability and long-term benefits of this strategy. It demonstrated that 2 hours of active therapy while the heart was exposed to light resulted in significant functional benefit and preserved ventricular architecture 4 weeks later. This has significant clinical implications in that it indicates SE therapy could be employed as an immediate adjunct to current medical interventions for patients suffering a myocardial infarction.

Although extremely different from any known strategy addressing myocardial ischemia, the use of SE to create a symbiotic photosynthetic relationship with ischemic cardiomyocytes represents a novel and feasible approach to treating the ischemic heart. Because SE is simple to genetically engineer, there are countless possibilities regarding the augmentation of energy production, in vivo tracking, and growth control. The data provide a very real benefit from the use of photosynthesis to treat ischemic disease. Additionally, the ability to treat ischemic tissue without the need for blood flow has far reaching implications beyond just the ischemic heart. As a result, the next stage of developing this photosynthetic strategy will focus on elucidating and proving mechanisms coupled with enhancing clinical translatability.

Methods

Isolation of SE. One frozen SE vial (Life Technologies, Cat#: A14259) was transferred from the −80° C. freezer onto dry ice. 30 ml of room temperature Gibco BG-11 medium (Life Technologies, Cat# 288 A1379902) was added to one baffled bottom flask with vented cap (Thermo Scientific, Cat#: 289 4116-0125). Cells were quickly thawed in a 35° C. water bath without agitating the vial. The full content was transferred into a flask containing culture media. The culture was placed on a rotating incubator (Thermo Electron Corp. Model#: 420) running at 34° C. and 125 rpm. A lamp with two 18" plant fluorescent light bulbs (GE F18T8 PL/AQ) was placed on the incubator to allow light to reach the culture. Initial outgrowth of the culture took 5-7 days. The culture was maintained by diluting down to 25% with fresh media every 4 days thereafter.

Rat Model of Acute Myocardial Ischemia and Ischemia-Reperfusion. Male Wistar rats, 300-350 g, were sedated in an isoflurane chamber, intubated with a 16G angiocatheter, and mechanically ventilated (Hallowell, Pittsfield, Mass.) on 2.0% isoflurane maintenance. The right carotid artery was dissected free, and a SPR-869 pressure-volume catheter (Millar, Houston, TX) was introduced into the left ventricle (LV) via the carotid. A midline sternotomy was then performed, and the ascending aorta was dissected free for placement of a flow probe (Transonic, Ithaca, N.Y.) to continuously monitor cardiac output (CO). Baseline hemodynamics were then acquired in all animals. To induce myocardial ischemia, the LAD was permanently occluded with a 6-0 polypropylene suture 2 mm below the level of the left atrial appendage. After 15 minutes, hemodynamic data was collected, and animals were randomized (n=6 per group) to receive intramyocardial injections of either PBS or $1\times10_6$ SE directly to the ischemic territory. Hemodynamics were then serially acquired every 15 minutes for 45 minutes. For the ischemia-reperfusion model, the LAD was temporarily occluded, and the animals were randomized to receive saline control or SE at the same dose. The LAD was un-occluded after 60 minutes and reperfusion with an open chest was allowed to occur for 60 minutes prior to closing the chest and recovering the animal. Serum was collected at 24 hours to assess for troponin level. At 4 weeks, animals underwent cardiac MRI. Imaging was performed using a 7 Tesla VNMRS horizontal bore scanner (Varian Inc., Palo Alto, Calif.) with a shielded gradient system (400 mT/m). Both 2-chamber and 4-chamber cines were acquired. Functional and architectural analysis was performed in a blinded fashion. Following MRI, animals underwent LV catheterization for hemodynamic assessment as described.

Intramyocardial Oxygen Tension Acquisition. Phosphorescence lifetime measurements were performed using a PMOD-5000 phosphorometer (Oxygen Enterprises, Philadelphia, Pa.). The PMOD-5000 is a frequency domain instrument operating in the frequency range of 100-100,000 Hz. The measured phosphorescence lifetimes are independent of local phosphor concentration and insensitive to the presence of endogenous tissue fluorophores and chromophores. The excitation light was carried to the measurement site through one glass fiber bundle and the emission collected by another 3-mm-diameter glass fiber bundle (center-to-center distance of 6 mm). The emission was passed through a 695-nm long-pass glass filter (Schott glass) and detected by an avalanche photodiode (Hamamatsu). The resulting photocurrent was converted into voltage, amplified, digitized, and transferred to the computer for analysis. Data was acquired at baseline, the time of ischemia, 10 minutes following injection, and 20 minutes following injection.

Thermal Imaging. For thermal imaging to assess surface myocardial heat emission and examine metabolic activity, a FLIR® A655sc camera was utilized. Care was taken to maintain a constant body temperature with the use of a heating pad. Additionally, the camera was precisely placed and mechanically tabilized 30 cm above the chest. At 20 minutes, thermal images were acquired and then analyzed with FLIR® software to determine myocardial surface temperature.

Immunological Analysis and Flow Cytometry. Male Wistar rats were sedated and intravenously administered either saline or $5 \times 10^8$ cyanobacteria. Prior to administration, blood samples were acquired for flow cytometry to examine inflammatory markers. At 16 hours following administration, blood was acquired for culture and flow cytometry. This was repeated at 40 hours, 88 hours. Blood cultures were performed at the Stanford Animal Diagnostic Laboratory. Flow cytometry was performed by placing 100 µL of peripheral blood into BD Microcontainer tubes with Dipotassium EDTA. Blood was transferred into 5 ml polystyrene Falcon tubes with 4 ml ammonium chloride NaAcetate buffer and remained on ice for 10 minutes. The red blood cell lysis was repeated a second time. The pellet was rinsed in PBS+2% FBS and cells were stained for membrane proteins (CD19, CD8, CD11 b, Ly-6G) for 1 hour in a 4° cold room. Cells were resuspended in 200 µl and flow cytometry analysis was done on BD Biosciences LSR 2 in the Stanford Shared FACS Facility.

Immunohistochemistry and Histology. At 4 weeks post-therapy for immunohistochemistry, hearts were explanted and immediately flushed with PBS, injected retrograde with Tissue Tek OCT (Sekura, Netherlands), frozen at −80° C., and sectioned onto glass slides using a Leica CM3050S cryostat (Leica, Wetzlar Germany) at a thickness of 10 µm. Next the samples were fixed with 4% paraformaldehyde and blocked with 10% fetal bovine serum. All sections were stained with cardiac troponin primary antibody at 1:200 dilution (Abcam, ab47003), a FITC secondary antibody (ab6717) at a 1:200 dilution, and counterstained with DAPI (Vector Labs). The sections were imaged with a Leica DM5000B fluorescent microscope. The SE are fluorescent at the 596 nm red channel of the scope.

For histology, hearts were explanted, flushed with PBS, and then injected retrograde with OCT through the aorta and pulmonary artery. Hearts were submerged in OCT, frozen, and stored in a −80° C. freezer. They were then stained with hematoxylin and eosin for assessment of abscess presence.

Animal Care. All experiments pertaining to this investigation conformed to the "Guide for the Care and Use of Laboratory Animals," published by the US National Institutes of Health (Eighth Edition, 2011).

Statistical Analysis. All analyzed variables approximated a normal distribution, and values for continuous variables were reported as means±standard deviation. Pair-wise Student's t-tests were used to compare continuous variables between groups. Statistical significance was determined to be $p<0.05$.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for correction of a metabolic imbalance as a result of ischemia in a mammalian tissue, the method comprising:
   contacting a tissue suffering from ischemia or at risk of ischemia with effective dose of a photosynthetic microorganisms in the presence of a light source, where the dose or concentration is sufficient to increase oxygenation and simple sugar delivery at the targeted tissue or organ, wherein the tissue is cardiac tissue that is ischemic as the result of a surgical procedure.

2. The method of claim 1, wherein an artificial light source is provided.

3. The method of claim 1, wherein an artificial light source is integrated into a device to isolate the photosynthetic microorganisms.

4. The method of claim 2, wherein an artificial light source is operably connected to the tissue being treated.

5. A method for correction of a metabolic imbalance as a result of ischemia in a mammalian tissue, the method comprising:
   contacting a tissue suffering from ischemia or at risk of ischemia with effective dose of photosynthetic microorganisms in the presence of a light source, where the dose or concentration is sufficient to increase oxygenation and simple sugar delivery at the targeted tissue or organ, wherein the tissue is cardiac tissue that is ischemic as the result of a surgical procedure, wherein the tissue is contacted with an effective dose of photosynthetic microorganisms systemically administered in vivo.

6. The method of claim 5, wherein the photosynthetic microorganism is a cyanobacteria.

7. The method of claim 6, wherein the cyanobacteria is a *Synechococcus*.

8. The method of claim 7, wherein the cyanobacteria is *Synechococcus elongates*.

9. The method of claim 6, wherein the cyanobacteria is a naturally occurring organism.

10. The method of claim 6, wherein the cyanobacteria is genetically engineered or selected for a trait of interest.

* * * * *